United States Patent [19]

Peyman et al.

[11] 4,238,482

[45] Dec. 9, 1980

[54] INTRAOCULAR INFUSION IRRIGATION SOLUTION AND METHOD

[76] Inventors: Gholam A. Peyman, 535 N. Michigan Ave., Chicago, Ill. 60611; Donald R. Sanders, 8110 N. Harding, Skokie, Ill. 60076

[21] Appl. No.: 947,225

[22] Filed: Sep. 29, 1978

[51] Int. Cl.$^3$ ................ A61K 31/735; C08B 37/02
[52] U.S. Cl. ................................. 424/180; 536/112
[58] Field of Search ..................... 536/112; 424/180

[56] References Cited

U.S. PATENT DOCUMENTS

| | | | |
|---|---|---|---|
| 2,988,482 | 6/1961 | Novak et al. | 536/112 |
| 3,262,847 | 7/1966 | Flodin et al. | 536/112 |
| 4,039,662 | 8/1977 | Hecht et al. | 536/112 |

*Primary Examiner*—Johnnie R. Brown
*Attorney, Agent, or Firm*—Dulin, Thienpont & Potthast, Ltd.

[57] ABSTRACT

Improved fluid for intraocular infusion and irrigation and methods of preparation and use. The fluid is an aqueous physiologic saline solution containing from 2–15% by weight of an artificial, substantially non-antigenic oncotic agent of a colloid type, such as dextran having an average molecular weight in the range of from about 1,000 to 40,000. The solution also contains NaCl, CaCl$_2$, dextrose and sodium bicarbonate, and is adjusted to have an osmolarity in the range of 260–400 mOsm/L and a pH in the range of from about 7 to 7.8. The solution may be used as a replacement fluid for the aqueous or vitreous humor, for the reestablishment of intraocular pressure during or after surgery, as an irrigating fluid during phacoemulsification, and generally for external eye surface rinsing during cataract surgery. The solution results in improved lens maintenance and corneal endothelial function during procedures such as vitrectomy, irrigation and aspiration of cataracts, and in phacoemulsification. Improvement is demonstrated, for example, by reduced corneal endothelial decompensation (inhibition of osmotic corneal swelling), by reduced water and sodium gain, by reduced potassium loss, and by recovery of the lens' ability to reverse electrolyte imbalances due to stress of the type typical of surgery, diabetes, ageing, and physical, chemical or biochemical trauma.

19 Claims, 17 Drawing Figures

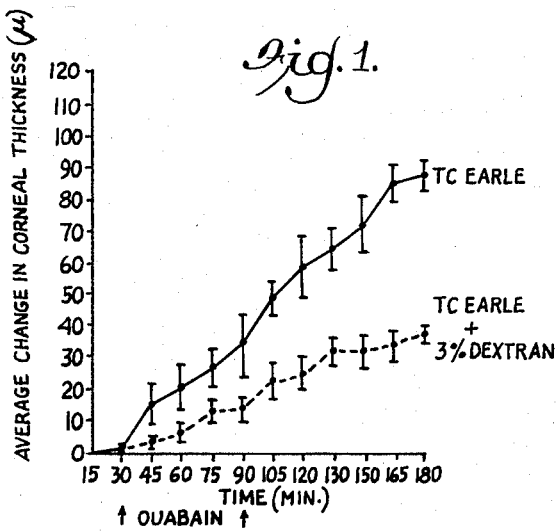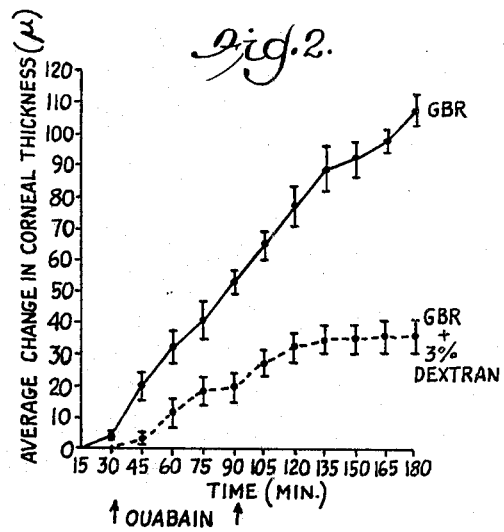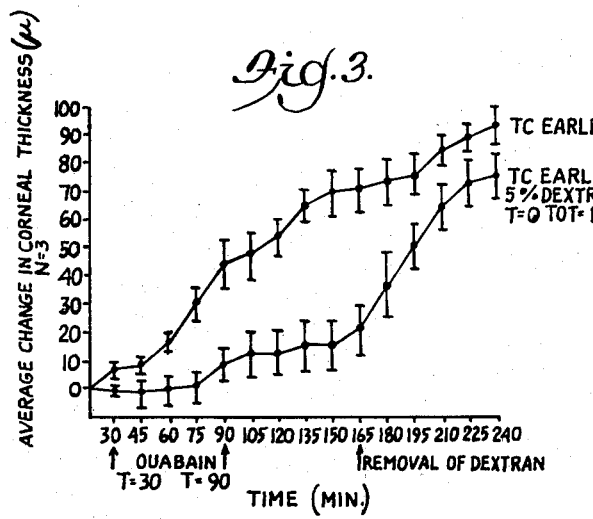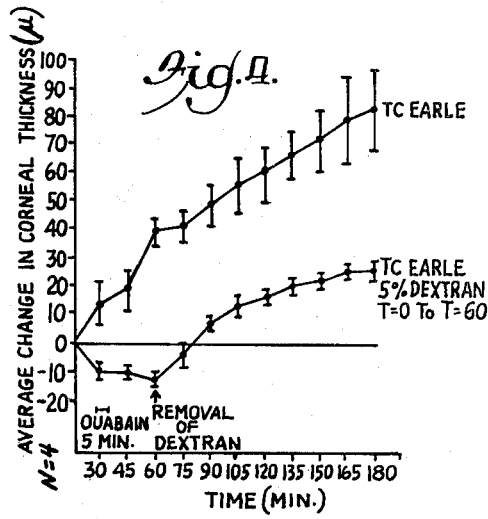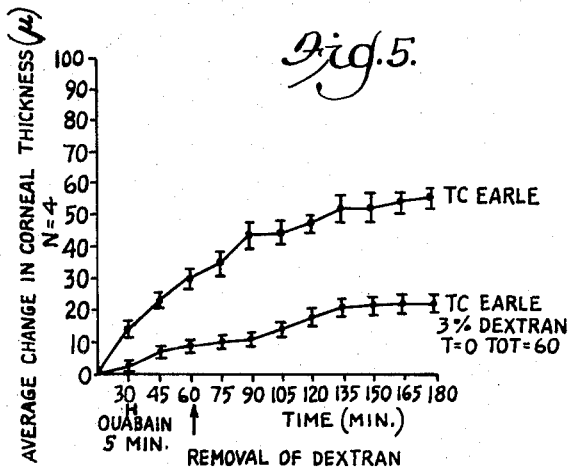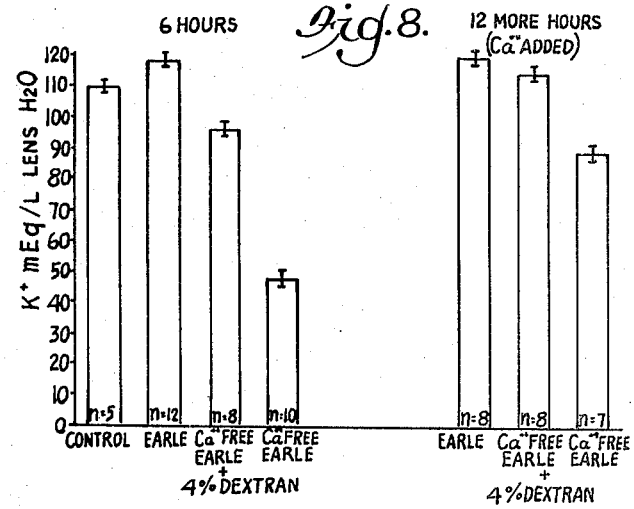

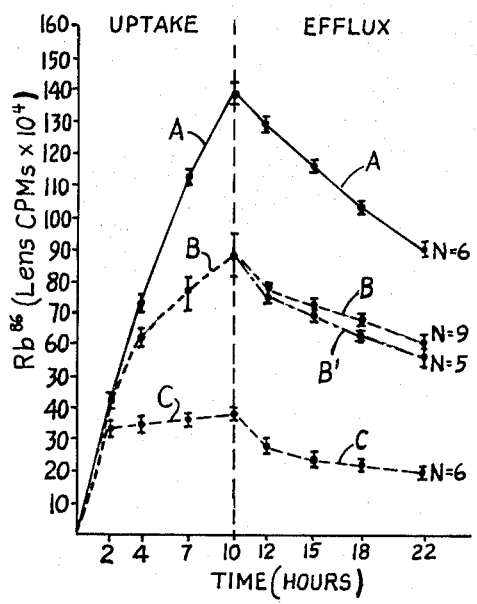
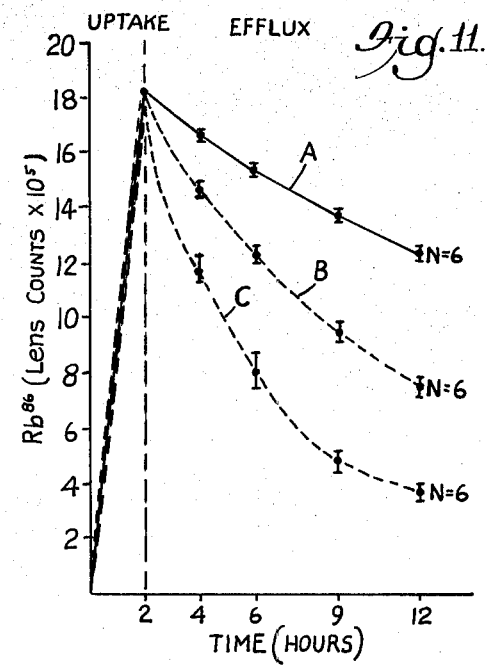
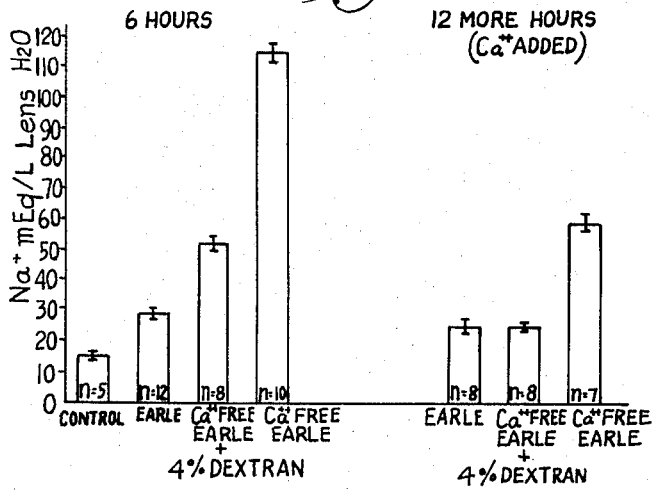
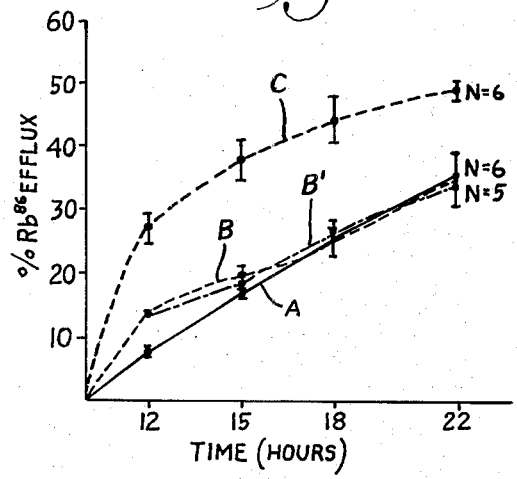
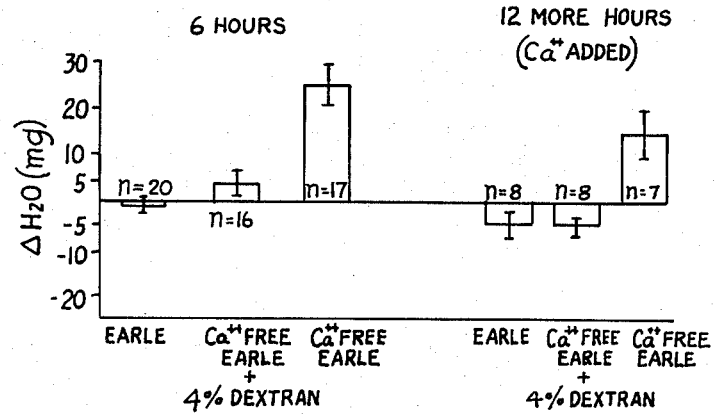

INTRAOCULAR INFUSION IRRIGATION SOLUTION AND METHOD

FIELD

This invention relates to improved intraocular infusion irrigation, maintenance and replacement fluids and their methods of use. More particularly, the invention is directed to the use of an artificial, substantially non-antigenic oncotic agent, such as dextran, in a physiologic saline solution to improve lens maintenance and corneal endothelial function which would normally be reduced as a result of stress-induced damage such as typical of eye surgery, diabetes, normal ageing, and physical, chemical or biochemical trauma.

BACKGROUND

There are an estimated 500,000 ocular surgical procedures (eye operations) being performed annually in the U.S. These include vitrectomy, irrigation and aspiration of cataracts, and phacoemulsification. In a substantial number of these, there occurs potentially damaging stress to the lens or corneal endothelium. This may result in irreversible harm to the lens or cornea, resulting in poor vision, necessitating a second operation, or use of heavy glasses if the lens has to be removed.

For some time a variety of solutions have been used for intraocular irrigation or infusion during such clinical procedures. The effect of the composition of such solutions on the corneal endothelium[1-5] and lens has been investigated.[3,6] There seems to be no doubt that a physiologic saline solution containing essential cations and glucose is a necessary minimum for short-term maintenance of the lens and corneal endothelial function. The use of bicarbonate as a buffer also appears helpful. The necessity for other additives such as adenosine and glutathione in a clinically useful infusion solution has been claimed, but has yet to be proved. The instability of these compounds in solutions may offset any possible advantage.

Although physiologic solutions maintain a normal environment for a healthy corneal endothelium and lens, conditions may differ if the endothelium or lens is under stress or is diseased, a situation often encountered in diabetic patients and older individuals.

Regarding extraocular use of dextran solutions, immersion of donor corneas in five percent dextran (mw 40,000) in tissue culture, TC 199 solution, (McCarey-Kaufman or M-K media) has been shown to be more effective than conventional eye bank techniques in preserving endothelial cell viability, as measured by temperature reversal studies, electron microscopy,[7,8] vital staining,[9] metabolic studies,[10] and corneal grafting in rabbits[11] and cats.[12] Its clinical value in maintaining eye bank corneas prior to keratoplasty has been demonstrated.[13-16] Corneas stored at 4° C. in this media do not swell to any great extent when compared to moist chamber-stored eyes.

However, to our present knowledge no studies have been published outside of our laboratory demonstrating the use of dextran as a component of an intraocular irrigation or infusion fluid. It is to be noted from the prior work with dextran that is was not considered for use inside an intact living eye. Further, solutions used for extraocular preservation (M-K or TC 199 solution) are complex tissue culture media containing amino acids and antibiotics. These solutions have the serious drawback of having a much greater tendency toward contamination. They are difficult to sterilize, a necessity for intraocular use, as they contain labile components, the amino acids and antibiotics. Likewise, the viscosity, toxicity, and the metabolic or excretory fate of dextran when used intraocularly was not known or predictable from such studies.

Accordingly, there is a need to provide an improved infusion and irrigation solution which can compensate for or help prevent, stress-induced lens and cornea damage during such clinical procedures as vitrectomy, irrigation and aspiration of cataracts, and phacoemulsification.

THE INVENTION

OBJECTS

It is among the objects of this invention to provide an improved intraocular infusion and irrigation fluid which employs an artificial, substantially non-antigenic oncotic agent, such as dextran, in a physiologically acceptable saline solution.

It is another object of this invention to provide an improved intraocular infusion and irrigation fluid which reduces corneal endothelial decompensation, inhibits colloidal swelling, inhibits osmotic swelling of lenses, inhibits stress-induced electrolyte and water imbalances, and reduces sodium gain, water gain and potassium loss.

It is another object of this invention to provide techniques for use of such fluid in eye surgery which results in improved cornea endothelium and lens viability.

Still other objects will be evident from the summary, detailed description and figures which follow.

SUMMARY

Surprisingly, we have discovered that use of an artificial, substantially non-antigenic oncotic agent, such as dextran, significantly improves the maintenance of lens and corneal function under stress conditions when used in an intraocular irrigation and infusion solution of the type described below. The addition of dextran as an oncotic (colloid osmotic) agent inhibits swelling and subsequent cell death in the cornea and lens which can decrease postoperative complications of intraocular surgery such as corneal edema or cataract. This discovery is particularly unexpected since the effect of dextran on normal cornea endothelium is minimal under normal physiologic conditions, but is extremely effective under a stress situation with a decompensated lens or corneal endothelium. The stress is situation is representative of that found in clinical situations.

Accordingly, the invention includes an improved fluid for intraocular infusion and irrigation and methods of preparation and use. The fluid is an aqueous physiologic saline solution containing from 2–15% by weight (gms/100 ml) of an oncotic agent of a colloid type comprising dextran having an average molecular weight in the range of from about 1,000 to 40,000. The more preferred ranges are 4–7 weight percent of dextran having a molecular weight of 5,000 to 10,000, with a 6% solution being particularly preferred and useful for the intraocular procedures and uses described herein.

Preferred ranges for the required components are:
Dextrose: >80 mg %
$CaCl_2$: pCa<3.0
$NaHCO_3$: 6–35 meq/L
Dextran:
2–15 weight %

1,000–40,000 M.W. (average)
Osmolarity: 260–400 mOsm/L
pH: 7.0–7.8
NaCl: adjusted for osmolarity, typically 6–7 g/L.
Specific examples of solutions and other components are given below.

FIGURES

The detailed description will have reference to the drawings in which:

FIGS. 1 and 2 show the effect on corneal thickness of 3% dextran added to two different solutions;

FIGS. 3, 4 and 5 show the effect on corneal thickness by the addition and removal of different concentrations (5% and 3%) solutions of dextran on corneas stressed for different amounts of time;

Figure 9A:
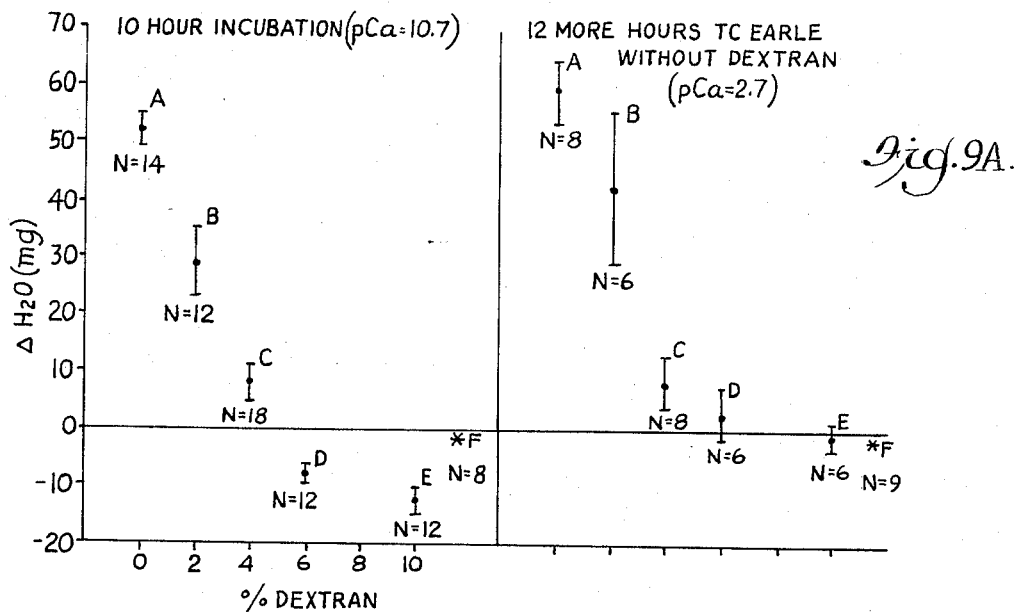
Figure 9B:
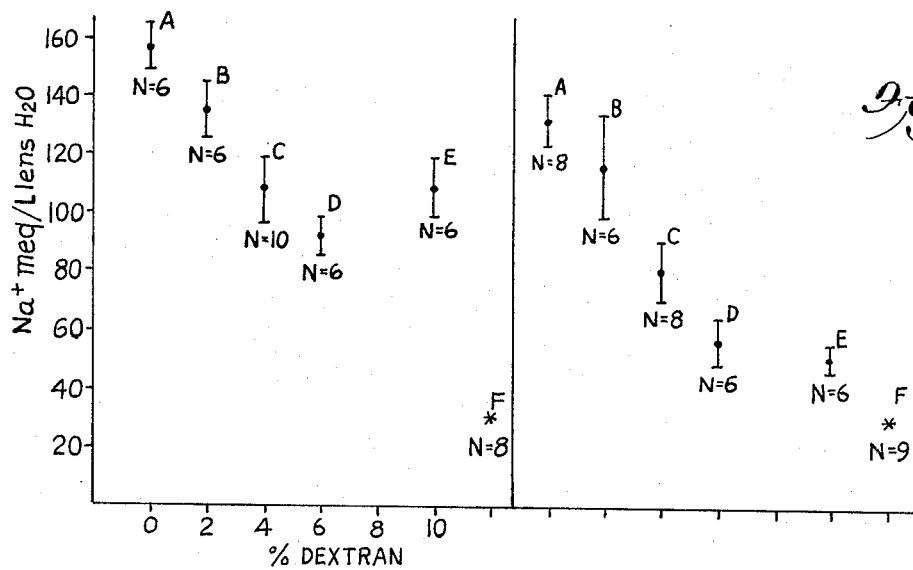
Figure 9C:
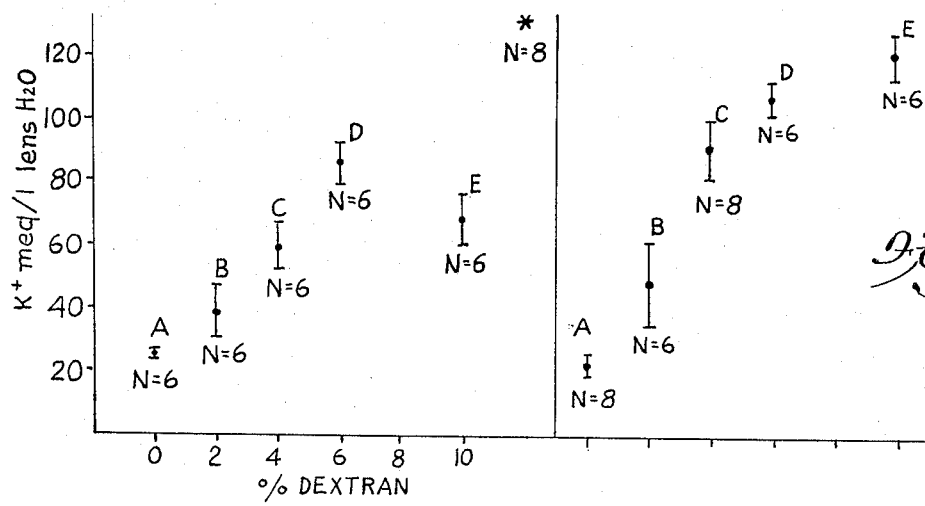
Figure 10:
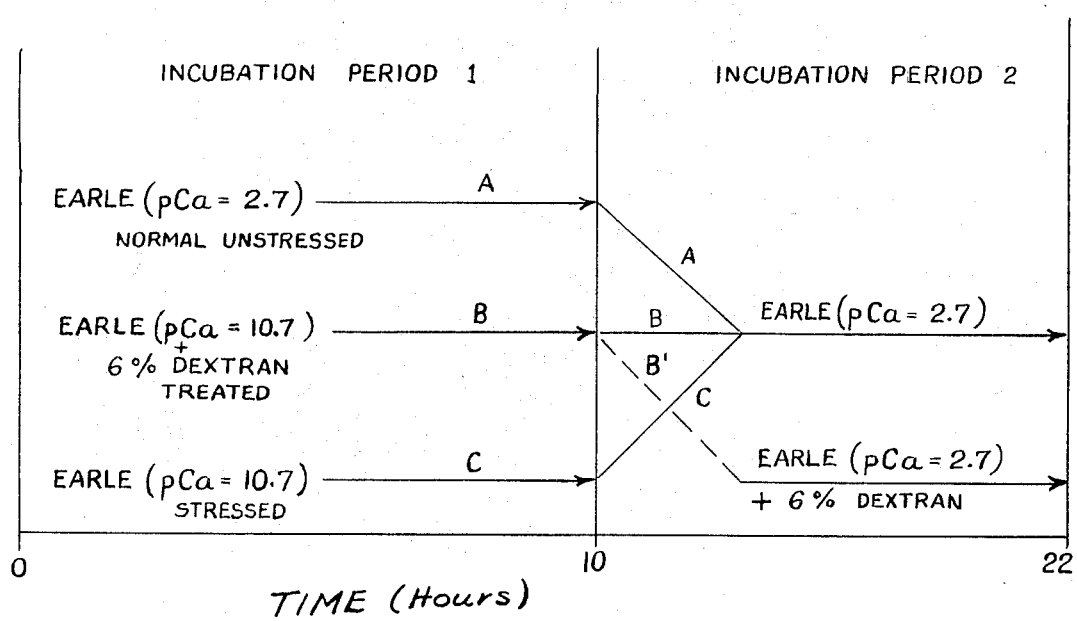
Figure 13:
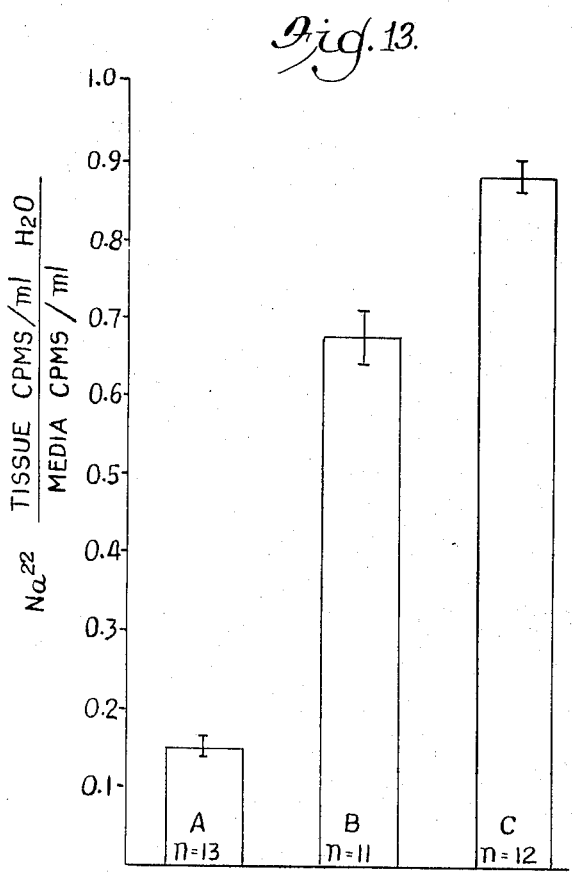
Figure 14:
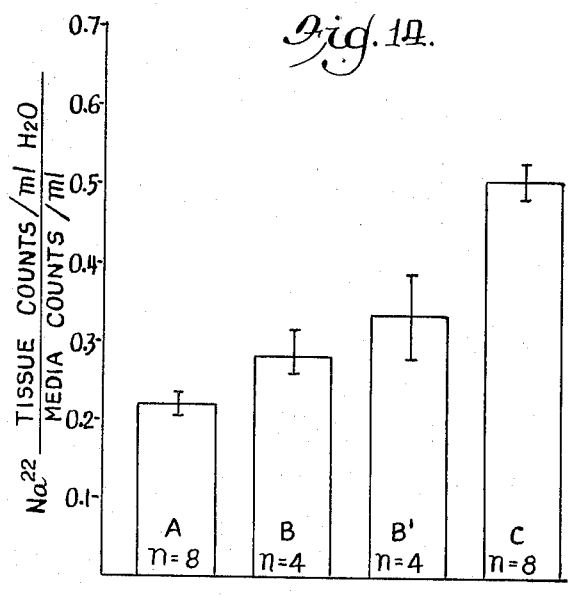

FIGS. 6, 7 and 8 demonstrate the change in lens water, $Na^+$ and $K^+$, respectively, after six hours incubation in $Ca^{+2}$-free media (to stress the lens), and after an additional 12 hours in $Ca^{+2}$ enriched media to show the recovery;

FIGS. 9A, 9B and 9C show a dextran dose (concentration) response curve, i.e., the effect of dextran concentration on the change in lens water (FIG. 9A), $Na^+$ concentration (FIG. 9B), and $K^+$ concentration in stressed lenses;

FIG. 10 shows schematic a protocol for radiosotope tracer studies;

FIG. 11 shows the effect of dextran on $Rb^{86}$ efflux;

FIGS. 12A and 12B show the effect of dextran on $Rb^{86}$ uptake and efflux, in absolute values (FIG. 12A) and in percentage efflux (FIG. 12B); and FIGS. 13 and 14 show the effect of dextran on inhibiting the accumulation of $Na^{22}$ in the lens, with FIG. 13 being accumulation after stressing, and FIG. 14 showing accumulation after attempted reversal of the stress.

DETAILED DESCRIPTION

The invention is described with more particularity herein with specific examples and tests being made by way of example and not by way of limitation of the principles of the invention.

EXAMPLE 1

The following table illustrates the preferred ranges of essential components of the intraocular infusion and irrigation solution of this invention, and a specific example of a generally useful solution. Dextran is a branched polysaccharide, and we prefer to use commercially available laboratory or biological grade dextran, for instance a low molecular weight hydrogenated dextran of the following molecular weight parameters: 50% less than 2000 mw, 42% greater than 2200 mw, 18% less than 1000 mw, and an estimated 32% between 1000 and 2000 mw, which dextran is available from Dextran Products, Ltd., Euless, Tx. 76039. For higher molecular weight dextran having an average molecular weight of 40,000, we prefer to use lab grade from Sigma Chemical, St. Louis, Mo. 63178.

TABLE 1

| Intraocular Infusion/Irrigation Solution | | |
|---|---|---|
| | Amount | |
| | General Range | Specific Solution |
| Essential Component | | |
| NaCl | adjusted to produce osmolarity range below, | |
| Dextrose | generally 6–7 g/ >80 mg % | 6–8 g/L 80–120 mg % |
| $CaCl_2$ | pCa <3.0 | .2 g/L |
| Buffer, e.g., $NaHCO_3$ | 6–35 meq/L | 2.4 g/L |
| Dextran | 2–15% by weight of about 1000–40,000 mw (average) | 6% (60 g/L), average MW40,000 |
| Osmolarity | 260–400 mOsm/L | ~300 mOsm/L |
| pH | 7.0–7.8 | 7.4 |
| Additional Components | | |
| KCl | physiologically acceptable range | .4 g/L |
| $MgSO_4$ $Mg^{+2}$ ion, e.g., $MgSO_4$ or $MgCl_2$ | | .2 g/L ($MgSO_4$) |

The above solutions are used in intraocular surgical procedures, including vitrectomy, irrigation and aspiration of cataracts, phacoemulsification, washing of the eye during cataract surgery, replacement of aqueous and vitreous fluid, and reestablishment of intraocular pressure during or after surgery. No toxicity was observed during a 21 day postoperative observation period, a period during which molecules having the size and solubility characteristics of the dextran should have been completely eliminated from the eye.

EXAMPLE II

Corneal clarity and thickness are sensitive indices of an intact and viable endothelial cell layer. Although some damage to this cell layer is inevitable in any intraocular procedure, the degree of endothelial decompensation in a procedure is reflected in the postoperative increase in corneal thickness. During vitrectomy, the corneal endothelium is exposed to infusion solution for as long as 60 minutes. Corneal edema may be a subsequent complication. In this example, we evaluated the use of low molecular weight dextran in vitreous replacement fluid to demonstrate that its presence inhibits corneal edema after vitrectomy.

We studied with pachometry the degree of corneal endothelial decompensation in rabbits undergoing extracapsular lens extraction and vitrectomy. Vitrectomy and intraocular infusion were performed for one hour in the three test groups, following an extracapsular lens extraction and the rabbits underwent extracapsular extraction alone in the control eyes. Vitrectomy and replacement of the vitreous humor with an intraocular infusion solution containing dextran in accord with this invention demonstrated the least overall increase in corneal thickness. This demonstrates that the use of dextran in accord with this invention functions to inhibit colloidal swelling, a major factor potentiating corneal endothelial damage. The following description of the procedures was earlier reported by us in Annals of Opthalmology, October, 1977, pp. 1241–1244.

Twelve albino rabbits, each weighing approximately 2 to 3 kg. were used in this study. After preliminary indirect and direct ophthalmoscopy, one of us (G.A.P.) measured the corneal thickness of each rabbit eye. The same Haag-Streit pachometer and Haag-Streit slit lamp were used in all measurements. We used the following settings: objective magnification, X1; slit beam intensity, 6 volts; angle between light beam and microscope, 35 degrees. After careful pachometric evaluation, the rabbits were divided into 4 groups of 3 each and subjected to surgery.

All 4 groups (24 eyes) underwent surgical extracapsular lens extraction in the following manner. After anesthesia with intramuscular atropine and intravenous sodium pentobarbital, the pupils were dilated with 1% cyclopentolate hydrochloride and 10% phenylephrine hydrochloride. A temporal canthotomy was performed. Traction sutures were applied to the isolated rectus muscles. With a No. 15 blade, a corneolimbal incision was made and enlarged with corneoscleral scissors. After the anterior capsule was incised, the lens was exposed and expressed. The incision was closed with a running suture of 9-0 nylon.

Three groups of rabbits (6 eyes each) then underwent immediate pars plana vitrectomy. (The fourth group served as controls.) A 140 degree peritomy was performed. Approximately 3 mm behind the limbus, a 4 mm limbus-parallel sclerotomy was made, and a 5-0 chromic gut purse-string suture was inserted. Diathermy was applied to the choroid, and then the choroid was perforated with a No. 11 blade. The vitrophage was inserted through the sclerotomy until visualized behind the pupil. The sclerotomy suture was tightened and vitrectomy with removal of the lens capsule was done for 60 minutes. Each group of rabbits received vitreous humor replacement with 1 of 3 solutions (Table 2 below).

At the conclusion of the procedure, the vitrophage was withdrawn from the globe and the sclerotomy suture was immediately tightened. The conjunctiva and canthotomy were closed with 5-0 chromic gut. After ophthalmoscopic examination, atropine and Neosporin ointment were applied to each eye and then daily.

At intervals of 2, 5, 8, 11, 14, 17, and 20 days postoperatively, the corneal thickness of each eye was measured (without knowledge of the animal's operative history). On the 21st post-operative day, the animals were sacrificed.

The chemical compositions of the 3 vitreous infusion solutions used in the investigation are summarized in Table 2. The dextran solution was not evaluated for antigenicity.

TABLE 2

Chemical Composition of the Three Vitreous Replacement Solutions

| Chemical Constituent | 0.9% Physiologic Saline (millimol/liter) | 0.45% NaCl +2.5% Glucose (millimol/liter) | 0.45% NaCl, 2.5% Glucose, 2% Dextran* (millimol/liter) |
|---|---|---|---|
| NaCl | 154 | 77 | 77 |
| Glucose | — | 139 | 139 |
| Dextran | — | — | 20 gm/liter* |
| Osmolarity (mOsm) | 286 | 266 | 275 |

*low molecular weight polymer, molecular weight approximately 10,000.

The corneal thicknesses of the rabbits in the experimental and control groups are listed in Table 3.

TABLE 3

Mean Corneal Thickness (mm)

| Day | Control | 2.5% Glucose, 0.45% Sodium Chloride and 2% Dextran Solution | 2.5% Glucose and 0.45% Sodium Chloride | Physiologic Saline (0.9% Sodium Chloride) |
|---|---|---|---|---|
| Preop | 0.451 | 0.462 | 0.450 | 0.438 |
| 2 | 0.565 | 0.590 | 0.590 | 0.603 |
| 5 | 0.586 | 0.670 | 0.691 | 0.793 |
| 8 | 0.561 | 0.685 | 0.753 | 0.801 |
| 11 | 0.510 | 0.613 | 0.715 | 0.696 |
| 14 | 0.465 | 0.560 | 0.653 | 0.635 |
| 17 | 0.463 | 0.531 | 0.601 | 0.560 |
| 20 | 0.456 | 0.502 | 0.545 | 0.530 |

All the experimental eyes undergoing both lens extraction and vitrectomy with any vitreous infusion solution demonstrated a marked increase in central corneal thickness. On the eighth postoperative day, each group of experimental eyes demonstrated their maximal thickness. The group receiving vitreous replacement with physiologic saline (0.9%) showed the greatest mean increase in corneal thickness of 0.363 mm. The vitreous replacement solution composed of 2.5% glucose and 0.45% sodium chloride demonstrated a mean increase of 0.303 mm over the original mean central corneal thickness. The dextran-treated eyes demonstrated the lowest mean increase in central corneal thickness of only 0.223 mm.

Corneal edema and the resultant decrease in visual acuity may be common complications of cataract extraction, phacoemulsification and vitrectomy. Edelhauser and co-workers[1] reported physiologic saline (0.9%) and lactated Ringer's solution, both commonly employed as vitreous infusion solutions, to cause extensive degenerative change and increased corneal thickness in vitro.

Without being bound by theory, it appears that the low molecular weight dextran used as a hyperoncotic agent in the vitreous replacement solution of this invention acts to withdraw and prevent fluid uptake in the cornea, thus preventing degeneration of these cells.

In the control group, simple extracapsular lens extraction in the rabbit caused an increase in corneal thickness. On the fifth postoperative day, these 6 eyes demonstrated a maximal mean increase in central corneal thickenss of 0.13 mm, or approximately a 30% increase over their preoperative measurement. These corneas returned to their normal preoperative thickness by the end of the 3 week observation period, which suggests a transient and reversible degree of corneal endothelial decompensation with this procedure.

While all experimental eyes undergoing extracapsular lens extraction and pars plana vitrectomy demonstrated an increase in central corneal thickness, the 6 eyes infused with a dextran-containing intraocular infusion solution in accord with this invention had the least overall increase in corneal thickness. At the conclusion of the study, these 6 eyes returned to within 10% of their original preoperative corneal thickness. These values demonstrate a significant and surprisingly lesser degree of corneal endothelial decompensation than with vitreous replacement with either 0.9% sodium chloride or 0.45% sodium chloride and 2.5% glucose (neither solution including dextran).

EXAMPLE III

In this example, we studied the effect of dextran as an oncotic agent on corneal swelling using a specular microscope. This example demonstrates the beneficial use of physiologic intraocular infusion fluids containing dextran on corneal endothelium under a stress situation. Because of unavailability and variability of results with old human corneas, ouabain, a $Na^+$—$K^+$ATPase inhibitor, was used to stress animal corneas. The corneas were stressed by addition of $10^{-5}$ M ouabain to the infusion fluids for various time intervals. Ouabain inhibits the biochemical pump that removes water from the cornea. Dextran in Earle and GBR solutions significantly inhibited swelling of functionally impaired corneas. However, when the dextran was removed from the solution, the corneas swelled rapidly to reach the level of those incubated in ouabain without dextran. When the corneas were stressed in ouabain for a short period of time, dextran had a protective effect that lasted even after its removal from the solution.

Corneas obtained from 2- to 4-kg albino rabbits were prepared in the manner described by Dikstein and Maurice[17] and mounted in a dual-chambered specular microscope. The epithelium was left intact and covered with silicone oil. All perfusions were carried out with paired corneas from the same albino rabbit and under identical conditions of temperature (36° to 37° C.) and pressure (15 to 20 mm Hg).

Two basic infusion media were employed. The components of these media tissue culture (TC) Earle solution and glutathione-bicarbonate-Ringer's solution (GBR) are listed in Table 4.

TABLE 4

| | Infusion Media | |
|---|---|---|
| Chemical Composition | TC-Earle, gm/liter | GBR**, gm/liter |
| 1. NaCl | 6.800 | 6.520 |
| 2. Dextrose | 1.000 | 0.903 |
| 3. KCl | 0.400 | 0.362 |
| 4. CaCl$_2$ (anhydrous) | 0.200 | 0.115 |
| 5. MgSO$_4$ | 0.200 | 0.000 |
| 6. MgCl$_2$6H$_2$O | 0.000 | 0.159 |
| 7. NaH$_2$PO$_4$H$_2$O | 0.125 | 0.119 |
| *8. Glutathione | 0.000 | 0.0092 |
| *9. Adenosine | 0.000 | 0.0134 |
| *10. NaHCO$_3$ | 2.2 | 2.453 |
| Osmolarity (mOsm) | 295 | 300 |
| pH | 7.45 | 7.4 |

*Unstable components
**GBR indicates glutathione-bicarbonate-Ringer's solution

The TC Earle solution was obtained from a commercial source (manufacturer Difco Laboratories, Detroit, MI.), and the GBR was prepared fresh. Gentamicin (4 µg/ml) was added to each solution. The unstable components of GBR were added fresh at the time of infusion; the pH and osmolarity were also checked at this time.

EXAMPLE III—PART I

A: The corneas were perfused in a GBR or TC Earle base solution for a total of 180 minutes with three corneal thickness measurements being taken every 15 minutes and averaged. The only difference between paired corneas was the addition of 3% dextran (average molecular weight, 40,000) to one of them. From time t=30 minutes to t=90 minutes, all the fluids contained $10^{-5}$ M ouabain.

B: The corneas were perfused in TC Earle base solution for a total of 240 minutes with three corneal thickness measurements being taken every 15 minutes and averaged. The only difference between paired corneas was the addition of 5% dextran (average molecular weight 40,000) to one of them from time t=0 minutes to t=165 minutes. From time t=30 minutes to t=90 minutes, all fluids contained $10^{-5}$ M ouabain.

EXAMPLE III—PART II

A: The corneas were perfused in TC Earle base solution for a total of 180 minutes. The only difference between paired corneas was the addition of 5% dextran from time t=0 to t=60 minutes. Ouabain $10^{-5}$ M was in all fluids from time t=30 minutes to t=35 minutes.

B: The experimental design was identical to that in Part 2A except that a 3% concentration of dextran was used.

EXAMPLE III—RESULTS

Part 1A—The effect on corneal thickness of the addition of dextran to TC Earle and GBR solutions in corneas stressed with ouabain for one hour is illustrated in FIGS. 1 and 2. The solutions containing dextran demonstrated significantly less corneal swelling. Corneas incubated in TC Earle solution without dextran swelled 87µ in three hours as compared to only 37µ when 3% dextran was present. The 95% confidence interval for the difference between these groups is 40 to 60µ in three hours. Corneas incubated in GBR solution swelled 108µ in three hours as compared to 37µ with dextran in the perfusion media. The 95% confidence interval for the difference between these groups is 56 to 86µ in three hours.

Part 1B—The effect on corneal thickness of the addition then removal of dextran to TC Earle solution in corneas stressed with ouabain for one hour is illustrated in FIG. 3. Corneas incubated in TC Earle solution without dextran swelled 71µ in 165 minutes while during the same period those incubated in dextran swelled only 22µ. However, when the dextran was removed the swelling rate of the dextran-incubated corneas substantially increased, whereby the corneal thickness values of this group and the nondextran-incubated group were not significantly different at three hours (P>0.2).

Part 2A—The effect on corneal thickness of addition then removal of 5% dextran to TC Earle solution in corneas stressed with ouabain for five minutes is shown in FIG. 4. Corneas incubated in 5% dextran for the first hour deswelled 14µ while those without dextran swelled 39µ. Upon removal of the dextran the swelling rate was 29 µ/hr for the first hour decreasing to a swelling rate of 10 µ/hr for the second hour. The total corneal swelling over the three hour incubation was profoundly decreased (26µ) compared to the control not incubated in dextran (83µ). The 95% confidence intervals for the differences between these groups was 29 to 86µ in three hours.

Part 2B—The effect on corneal thickness of addition then removal of 3% dextran to TC Earle solution in corneas stressed with ouabain for five minutes is shown in FIG. 5. Corneas incubated in 3% dextran swelled 9µ in the first hour, while those without dextran swelled 30µ. Upon removal of the dextran the swelling rate averaged only 6 µ/hr over the next two hours. The total corneal swelling over the three hour incubation was only 22µ compared to 53µ for the control group not incubated in dextran. The 95% confidence intervals for the difference between these groups was 22 to 40μ in three hours.

Although physiologic solutions maintained a normal environment for a healthy corneal endothelium, conditions may differ if the endothelium is under stress or diseased, a situation often encountered in diabetic patients and older individuals. For this reason, we compromised the endothelial cell function by addition of ouabain, a cardiac glycoside inhibiting the $Na^+$—$K^+$ATPase pump.

Part 1A of our study demonstrates that dextran is capable of inhibiting swelling in ouabain stressed corneas. Part 1B, however, shows that upon removal of the dextran swelling is accelerated so that the final corneal thickness is equivalent whether dextran is used or not. We interpreted this swelling as evidence of severe toxicity from prolonged (one-hour) incubation in ouabain. This portion of the experiment demonstrated that dextran could inhibit oncotic swelling in spite of extensive functional impairment of the endothelial cells.

To determine whether dextran can exert a protective effect in functionally compromised but still viable endothelial cells, we incubated corneas in ouabain for only five minutes and tested the effect of incubation with and removal of 3% and 5% dextran part 2A and B) (FIGS. 4 and 5). In both of these studies the addition of dextran for one hour substantially decreased the total swelling and swelling rate during a three hour period, which demonstrated a true protective effect on endothelial pump function. Interestingly, corneas incubated with 5% dextran deswelled initially whereas those incubated in 3% dextran swelled slightly, indicating that the colloid osmotic pressure of the corneal stroma lies somewhere between these values.

EXAMPLE IV

The search for an ideal intraocular irrigation solution is of paramount importance to the ophthalmic surgeon. If a solution can be found that not only supports lens and corneal endothelial functioning under physiologic conditions but that also exerts a protective effect under a stress situation, then the development of postoperative cataract or corneal edema can possibly be minimized. This example describes the effect of dextran as a component of an intraocular infusion/irrigation solution upon lens function in lenses stressed by incubation in $Ca^{++}$-free media.

Preliminary experiments demonstrate that dextran in intraocular solution is capable of inhibiting osmotic swelling of lenses damaged by a surface active cationic detergent cetylpyridinium chloride. This example extends that study by demonstrating that when lenses are incubated in calcium-free media for six hours they swell and show marked electrolyte imbalances (a high sodium and low potassium) some of which is irreversible. Addition of a 4% dextran (average molecular weight=40,000) solution in accord with the invention markedly decreases the swelling and electrolyte changes. When lenses are reincubated in calcium enriched media for 12 hours the electrolyte and water content are the same as if the lenses were never stressed or damaged by immersion in calcium-free media. Dextran substantially inhibited lens swelling, $Na^+$ gain, and $K^+$ loss caused by six-hour incubation in $Ca^{++}$-free media. Following an additional 12-hour incubation in $Ca^{++}$ enriched media, the water and electrolyte balance in the dextran incubated group was essentially the same as lenses never exposed to a $Ca^{++}$-free media. Those lenses not incubated in dextran demonstrated significant residual lens swelling and electrolyte imbalance. It is concluded that dextran-containing solutions in accord with this invention inhibit colloid osmotic swelling and exert a protective effect upon lens function under a stress situation.

Albino rabbits, weighing 2 to 3 kg were killed with pentobarbital sodium injection and both eyes enucleated immediately. The lenses were obtained by opening the eyes at the posterior pole, gently separating the vitreous humor to the side, and separating the zonules with curved blunt scissors.

Incubation in $Ca^{++}$-free media

The lenses were isolated, weight, and placed in modified Kjeldahl flasks containing 15 ml of one of the following solutions and incubated at 37° C. in a shaking water bath.
1. Tissue culture (TC) Earle solution.
2. $Ca^{++}$-free TC Earle solution.
3. $Ca^{++}$-free TC Earle solution plus 4% dextran (mw, 40,000).

All lenses were reweighed immediately following a six-hour incubation, and half of the lenses from each group were dried at 100° C. for 24 hours, reweighed, then placed in screw-capped tubes with Teflon-coated liners to which 1 ml of fuming nitric acid was added. The lenses were digested in the nitric acid for two hours at 37° C. and $Na^+$ and $K^+$ content determined by flame photometry. The remaining lenses from each group were transferred to Kjeldahl flasks containing Earle's solution with calcium (plus 4% dextran in group 3) and incubated for an additional 12 hours. Then water, $Na^+$, and $K^+$ data were collected as described above.

RESULTS

FIGS. 6, 7 and 8 demonstrates the change in lens water, $Na^+$, and $K^+$ after six hours' incubation in $Ca^{++}$-free media and after an additional 12 hours in $Ca^{++}$-enriched media. Control lenses incubated in Earle solution demonstrated essentially no change in water content and showed normal $Na^+$ and $K^+$ concentrations after six hours. They lost an average of 5 mg of water and continued to maintain normal electrolyte concentrations after 18 hours. Lenses incubated in $Ca^{++}$-free Earle solution exhibited a profound increase in water content (mean=24.7 mg) after six hours and a gross electrolyte imbalance with an elevated $Na^+$ (115 meq/liter) and decreased $K^+$ (48 meq/liter). After an additional 12 hours in $Ca^{++}$-free media the lenses lost some of the water they had gained but still had a mean net increase of 14 mg of water. The electrolyte imbalance improved but not completely. Lenses incubated in $Ca^{++}$-free media treated with dextran solution only gained an average of 4 mg of water after six hours and demonstrated a moderated increase in $Na^+$ (53 meq/liter) and decrease in $K^+$ (94 meq/liter). After 12 additional hours in $Ca^{++}$-enriched media there was virtually no difference in lens water, $Na^+$, and $K^+$ between control nonstressed lenses and the dextran-treated lenses.

Normal lens volume and electrolyte concentration are maintained by a dynamic equilibrium between a membrane-localized metabolically dependent cation pump and impermeable anionic molecules. The intracellular macromolecules consist primarily of $\alpha$, $\beta$, and $\gamma$ crystallins, organic phosphates, and RNA, and they exert an internal colloid osmotic (oncotic) pressure. If this pressure were unopposed, it would cause the lens fibers to swell until the fiber membranes and lens capsule either became permeable to the multivalent anions, ruptured, or exerted an opposing hydrostatic force sufficient to inhibit further swelling.

Under normal conditions, it is the lens cation pump that opposes the colloid osmotic pressure of the intracellular anions. By maintaining sodium and potassium at unequal concentrations on opposite sides of the lens membranes, the pump renders these membranes functionally impermeable to cations. These functionally impermeable cations, in effect, exert a "colloid" osmotic pressure exactly equal and opposite to that produced by the intracellular impermeable anions, and so inhibit swelling. The ability of the metabolically dependent cation pumping mechanism to maintain this functional membrane impermeability can be destroyed by poisoning the pump or by increasing the membrane permeability to cations sufficiently to overcome it. Failure of the cation pump with unopposed colloid osmotic swelling is a mechanism for lenticular intumescence.

Incubation of lenses in $Ca^{++}$-free media causes substantial water and electrolyte imbalances, presumably due to increased membrane permeability and dissociation of tight junctional complexes between cells. These changes are partially reversible as calcium is replaced in the media. The portion that is irreversible is probably due to the permanent lens fiber damage caused by colloid osmotic swelling. The addition of the dextran in accord with the invention to the $Ca^{++}$-free media exerts an oncotic pressure opposing lens swelling and partially inhibiting the permeability changes to electrolytes. When the oncotic swelling is inhibited, the water and electrolyte changes induced by immersion of lenses in $Ca^{++}$-free media are completely reversible as shown in FIGS. 6 through 8. Thus, the addition of dextran in accord with the invention can inhibit colloidal swelling, a major factor potentiating lens damage from a variety of insults, and exerts a protective effect upon lens function under a stress situation.

EXAMPLE V

This example establishes a dose response curve for stressed lenses, and demonstrates the effect of dextran-containing solutions in accord with this invention on lens water, and sodium gain, and potassium loss (FIGS. 9A–C). This experiment shows that a 6% concentration of dextran in a solution in accord with the invention is most effective in inhibiting the lens damage caused by immersion in $Ca^{++}$-free media. Radioactive rubidium (which the lens treats like potassium) uptake and efflux studies and sodium uptake studies (FIGS. 10–14) showed that lenses incubated in dextran solutions were less permeable to sodium and rapidly recovered the ability to actively reverse electrolyte imbalances when reincubated in $Ca^{++}$-containing media. In all of these figures N represents the number of lenses tested.

FIG. 9A shows the effect of dextran concentration on change in lens water; FIG. 9B shows the same on $Na^+$ concentration; and FIG. 9C shows the effect on $K^+$ concentration. Lenses in groups A, B, C, D, and E were incubated for 10 hours in low $Ca^{++}$ media (pCa=10.7) to stress them with the only difference being the weight % dextran placed in the media. Group A=0% dextran, B=2%, C=4%, D=6%, and E=10%. Group F represented lenses placed in normal physiologic media. The $H_2O$, $Na^+$, and $K^+$ changes after this 10 hour incubation are shown on the left side of each figure. The lenses were then transferred after the 10 hour incubation to normal physiologic media (Earle's solution pCa=2.7) for an additional 12 hours. The $H_2O$, $Na^+$, and $K^+$ changes after the additional 12 hour incubation are shown on the right side of the figures. The use of dextran solutions or concentrations of 6% (group D) to 10% (group E) totally inhibited the water gain caused by incubation in low $Ca^{++}$ media. Also, the final lens $Na^+$ and $K^+$ concentrations tended more toward the normal concentrations found in Group F.

FIG. 10 shows in schematic the protocol for radioisotope tracer studies. Rabbit lenses were incubated during period #1 (T=0 to T=10 hours) in one of the three incubation media A, B, or C shown. They were then transferred to one of the two media shown in incubation period #2 (T=10 to T=22 hours).

FIG. 11 shows the effect of dextran upon $Rb^{86}$ efflux. $Rb^{86}$(1 μC/ml) was added to Earle's solution during a 2 hour preincubation period (this would be two hours prior to the zero point on the graph of FIG. 10). The lenses were then transferred to solutions A, B and C as shown in FIG. 10. The efflux, which is a measurement of lens leakiness (the greater the leakiness the more damaged the lens), in the dextran treated lenses (group B) is intermediate between the unstressed (group A) and the stressed group without dextran (group C).

FIGS. 12A and 12B show the effect of addition of dextran upon $Rb^{86}$ uptake and efflux. $Rb^{86}$(1 μC/ml) was added during the 10 hour incubation period (see FIG. 10). The more uptake demonstrated, the healthier the lens. The difference between lines B and C represents the beneficial effects of dextran allowing more Rb accumulation. The efflux is shown in absolute values on the right side of FIG. 12A, and in terms of % efflux in FIG. 12B. FIG. 12B demonstrates that two sets of lenses treated with dextran solutions in accord with the invention (lines B and B') have as low an efflux after the first two hours as lenses never stressed or damaged (line A). Line C represents those lenses not treated with dextran solutions, and they show more leakiness.

FIG. 13 shows the effect of dextran on accumulation of $Na^{22}$ in the lens during the initial incubation period 1 (See FIG. 10). The lower the tissue/media ration of $Na^{22}$ the healthier the lens. During the initial incubation the lenses treated with dextran solution (B) are still permeable to Na but less so than those lenses incubated without dextran (C). Normal lenses are group A.

FIG. 14 shows the effect of dextran on accumulation of $Na^{22}$ in the lens during incubation period 2 (See FIG. 10). The tissue/media ratio of lenses treated with dextran solution (B and B') is lower than lenses incubated without dextran (C) indicating a greater ability to transport Na out of the lens. Again normal lenses are group A.

It should be understood that various modifications within the scope of this invention can be made by one of ordinary skill in the art without departing from the spirit thereof. We therefore wish our invention to be defined by the scope of the appended claims as broadly as the prior art will permit, and in view of this specification if need be.

REFERENCES

1. Edelhauser, H., Van Horn, D., Hydiuk, R., Schultz, R. O.: Intraocular irrigating solution: Their effect on the corneal endothelium. Arch Opthalmol 93:648, 1975.

2. McCarey, B. E., Edelhauser, H. F., Van Horn, D. L.: Functional and structural changes in the corneal endothelium during the vitro perfusion. Invest. Opthalmol. 12:410–417, 1973.
3. Sanders, D. R., Peyman, G. A., McEnerney, J. K., Janevicius, R. V.: In vitro evaluation of intraocular infusion fluids: Effects on the lens and cornea. Ophth. Surg. 8:63, 1977.
4. McEnerney, J. K., Peyman, G. A.: Simplification of glutathione-bicarbonate ringer solutions: Its effects on corneal thickness. Invest. Ophthal.
5. McEnerney, J. K., Peyman, G. A., Janivicius, R. V.: A new irrigating solution for intraocular surgery: T. A. Earle solution. Ophthalmic Surg.
6. Christiansen, J. M., Kollarits, C. R., Tukuc, H., Fishman, M. C.: Intraocular irrigating solutions and lens clarity. Am. J. Ophthalmol. 82:594, 1976.
7. McCarey, B. E., and Kaufman, H. E.: Improved corneal storage. Invest Ophthalmol 13:165, 1974.
8. McCarey, B. E., Sakimoto, B., and Bigar, F.: Ultrastructure of M-K and refrigerated moist chamber stored corneas. Invest. Ophthalmol. 13:559, 1974.
9. Van Horn, D. L., Schultz, R. D., and Debruin, J.: Endothelial survival in corneal tissue stored in M-K medium. Am. J. Ophthalmol. 80:642, 1975.
10. Thoft, A. R., Friend, J., Freedman, H., and Dohlman, C. H.: Corneal epithelial preservation. Arch. Ophthalmol. 93:357, 1975.
11. Bigar, F., McCarey, B. E., and Kaufman, H. E.: Improved corneal storage: Penetrating keratoplasty in rabbits. Exp. Eye Res. 20:219, 1975.
12. Meyer, R. F., McCarey, B. E., Valenti, J., Gravenstein, N., and Kaufman, H. E.: Scanning electron microscopy of post-operative M-K and moist chamber-stored corneas. Invest. Ophthalmol. 15:260, 1976.
13. Bigar, F. Kaufman, H. E., McCarey, B. E., and Binder, P. S.: Improved corneal storage for penetrating keratoplasties in man. Am. J. Ophthalmol. 79:1115, 1975.
14. Stark, W. J., Maumanee, A. E., and Kenyon, K. R.: Intermediate term corneal storage for penetrating keratoplasty. Am. J. Ophthalmol. 79:795, 1975.
15. Aquavella, J. V., Van Horn, D. L., and Haggerty, J.: Corneal preservation utilizing the M-K medium. Am. J. Ophthalmol. 80:791, 1975.
16. McCarey, B. E., Meyer, R. F., and Kaufman, H. E.: Improved corneal storage for penetrating keratoplasties in humans. Ann. Ophthalmol. 8:1488, 1976.
17. Dikstein, S., Maurice, D.: The metabolic basis to the fluid pump in the cornea. J. Physiol. 22:29, 1975.

We claim:

1. An intraocular infusion and irrigation fluid comprising an aqueous physiologically acceptable saline solution containing from 2–15% by weight of an artificial, substantially non-antigenic, non-toxic oncotic pressure agent selected from a colloid-type dextran.

2. An intraocular fluid as in claim 1 wherein:
   (a) said dextran has an average molecular weight in the range of from about 1,000 to 40,000;
   (b) said solution has:
      (i) an osmolarity in the range of from about 260–400 mOsm/L; and
      (ii) a pH in the range of from about 7.0 to 7.8; and
   (c) said solution contains:
      (i) sodium chloride; and
      (ii) dextrose.

3. An intraocular fluid as in claim 2 wherein said solution includes:
   (a) a source of calcium ions, and
   (b) a physiologically acceptable buffer.

4. An intraocular fluid as in claim 3 wherein the pCa is less than 3.0.

5. An intraocular fluid as in claim 4 wherein said Ca ion source is $CaCl_2$.

6. An intraocular fluid as in claim 2 wherein said dextrose is present in an amount of greater than 80 mg%.

7. An intraocular fluid as in claim 3 wherein said buffer is sodium bicarbonate present in an amount in the range of from about 6–35 meg/L.

8. An intraocular fluid as in claim 2 wherein said NaCl is present in an amount of from 6–7 g/L.

9. An intraocular fluid as in claim 3 which includes KCl and a source of $Mg^{+2}$ ion.

10. An intraocular fluid as in claims 3 or 9 wherein said dextran is present in the range of from about 4 to 7 weight %, and said average molecular weight ranges from about 5,000 to 10,000.

11. An intraocular fluid as in claim 10 wherein said dextran is present in an amount of about 6% by weight.

12. An intraocular fluid as in claim 4 wherein:
   (a) said dextrose is present in an amount greater than 80 mg%;
   (b) said buffer is $NaHCO_3$ present in an amount in the range of from 6–35 meq/L;
   (c) said NaCl is present in an amount of from 6–7 g/L.

13. An intraocular fluid as in claim 12 wherein said dextran is present in the range of from about 4 to 7 weight %, and said average molecular weight ranges from about 5,000 to 10,000.

14. An intraocular fluid as in claim 13 wherein said dextran is present in an amount of about 6% by weight.

15. An intraocular fluid as in claim 14 which includes KCl and a source of $Mg^{+2}$ ion.

16. A method of reducing stress-induced damage to lenses and corneal endothelia during surgical vitrectomy, irrigation, cataract aspiration, and phacoemulsification, comprising the steps of:
   (a) providing an intraocular fluid as defined in claims 1 or 3; and
   (b) introducing said fluid intraocularly in an amount to maintain more nearly normal corneal endothelial and lens functions during said surgical procedures, as measured by at least one of:
      (i) reduction in corneal endothelial decompensation;
      (ii) reduced water gain;
      (iii) reduced sodium gain;
      (iv) reduced potassium loss; and
      (v) recovery of the lens ability to reverse stress-induced electrolyte imbalances.

17. Method as in claim 16 wherein said introduction step includes one or more of:
   (i) replacement, at least in part, of aqueous or vitreous humor;
   (ii) reestablishment of intraocular pressure during or after surgery; and
   (iii) ocular irrigation.

18. Method as in claim 17, wherein said irrigation is intraocular irrigation during phacoemulsification.

19. Method as in claim 16 wherein said fluid is an intraocular fluid comprising an aqueous physiologically acceptable saline solution containing 4–7 weight % of dextran, wherein:

(a) said dextran has an average molecular weight in the range of from about 5,00 to 10,000;
(b) said solution has:
  (i) an osmolarity in the range of from about 260–400 mOsm/L; and
  (ii) a pH in the range of from about 7.0 to 7.8; and
(c) said solution contains:
  (i) sodium chloride present in an amount of from 6–7 g/L;
  (ii) dextrose present in an amount greater than 80 mg%;
  (iii) a source of calcium ions;
  (iv) a physiologically acceptable $NaHCO_3$ buffer present in an amount in the range of from 6–35 meq/L; and
  (v) the pCa is less than 3.0.

* * * * *